(12) United States Patent
Falciani

(10) Patent No.: US 6,652,884 B2
(45) Date of Patent: Nov. 25, 2003

(54) METHOD FOR THE TREATMENT OF SOLID TUMORS BY ALBUMIN MICROPARTICLES INCORPORATING PACLITAXEL

(75) Inventor: Marco Falciani, Milan (IT)

(73) Assignee: ACS Dobfar S.p.A., Tribiano (IT)

( * ) Notice: Subject to any disclaimer, the term of this patent is extended or adjusted under 35 U.S.C. 154(b) by 69 days.

(21) Appl. No.: 09/835,384

(22) Filed: Apr. 17, 2001

(65) Prior Publication Data

US 2001/0046961 A1 Nov. 29, 2001

(30) Foreign Application Priority Data

May 17, 2000 (IT) ...................... MI2000A1107

(51) Int. Cl.[7] ............................ A61K 9/14; A61F 13/00; A61F 2/00; A61F 9/02
(52) U.S. Cl. ...................... 424/489; 424/422; 424/423; 424/436
(58) Field of Search ................. 424/489, 422, 424/423, 436

(56) References Cited

U.S. PATENT DOCUMENTS 5,916,596 A * 6/1999 Desai et al. ............... 424/489
6,096,331 A * 8/2000 Desai et al. ............... 424/422

FOREIGN PATENT DOCUMENTS

| WO | WO 94/18954 | 9/1994 |
| WO | WO 98/14174 | 4/1998 |
| WO | WO 00/06152 | 10/2000 |

OTHER PUBLICATIONS

U.S. patent application Ser. No. 09/835,384, Falciani, Apr. 17, 2001.

U.S. patent application Ser. No. 10/383,616, Zenoni, et al., Mar. 10, 2003.

U.S. patent application Ser. No. 10/383,639, Zenoni, et al., Mar. 10, 2003.

* cited by examiner

*Primary Examiner*—Thurman K. Page
*Assistant Examiner*—Humera N. Sheikh
(74) *Attorney, Agent, or Firm*—Oblon, Spivak, McClelland, Maier & Neustadt, P.C.

(57) ABSTRACT

The invention concerns a method for the treatment of tumors sensitive to Paclitaxel, by intra-arterial injections of dispersions of microparticles of albumin incorporating Paclitaxel in physiological solutions.

9 Claims, No Drawings

METHOD FOR THE TREATMENT OF SOLID TUMORS BY ALBUMIN MICROPARTICLES INCORPORATING PACLITAXEL

The invention relates to a method for the treatment of tumors sensitive to Paclitaxel, and more particularly concerns a method by which a significant remission or cure of the tumor, with very low toxic side effects, can be achieved by just a few infusions, each of short duration and spaced apart by some weeks.

Paclitaxel is a substance well known in the literature, with important clinical activity on a large number of tumors, such as ovary, lung, head and neck, bladder and breast tumors.

Paclitaxel is insoluble in water. In order to render it soluble and suitable for intravenous administration, it has been mixed with a surfactant (such as polyethoxylated castor oil, known by the registered name "Cremophor EL") and with about 50% of anhydrous alcohol USP, as vehicles for the Paclitaxel: this mixture was patented by Bristol-Myers Squibb and is known by the registered name "Taxol" to which reference will be made hereinafter, for simplicity. The presence of the surfactant and the anhydrous alcohol has serious drawbacks, such as strong hypersensitivity, in addition to other side effects.

In any event, Taxol is administered, and can be administered, only by intravenous injection, with very lengthy administration times in an attempt to minimize the toxic effects of the product.

To overcome the aforesaid drawbacks, the said Bristol-Myers Squibb has patented (European Patent Applications EP-A-0584001, EP-A0783885, EP-A-0783886 and U.S. Pat. No. 5,641,803 and U.S. Pat. No. 5,670,537) compositions equal to those of Taxol, but containing or combined with the use of medicaments able to impede serious anaphylactic reactions.

According to the known art, as described in the various patents, from 135 to 175 mg of Taxol per $m^2$ of the body surface are administered intravenously to patients subjected to therapy, each administration having a duration of about 3 hours: it is essential always to use the aforementioned pre-medications.

U.S. Pat. Nos. 5,439,686, 5,498,421 and 5,560,933 describe albumin microparticles incorporating the Paclitaxel: these particles are internationally identified by the symbols ABI 007, this denomination being used hereinafter for simplicity whenever reference is made to the aforesaid particles.

ABI 007 is a formulation of Paclitaxel stabilized by human albumin USP, which can be dispersed in directly injectable physiological solution.

Being free of toxic emulsifiers, ABI 007 can be administered with higher doses of Paclitaxel than in the case of Taxol, but this is currently done by the known method, i.e. by intravenous injection.

If ABI 007 in physiological solution is injected directly into the arteries which feed the territory associated with a tumor sensitive to paclitaxel, and is repeated several times at intervals of 3–4 weeks, it has been found that with this method a surprisingly favorable therapeutic result is obtained, i.e., a treatment response percentage which is higher than 71% (compared with the 40% achieved with the traditional treatment with paclitaxel, for example in treating head and neck cancer).

The invention hence relates to both the method of administrating Paclitaxel and the drugs usable to implement the method, i.e. drugs comprising a physiological solution in which ABI 007 is dispersed at a concentration between 2 and 8 mg/ml (preferably between 3 and 7.5 mg/ml) of the solution.

More particulary, the present invention relates to a method for the treatment of a patient afflicted with a tumor sensitive to paclitaxel, a method consisting of injecting into the artery feeding to the territory associated with a tumor a physiological solution containing between 190 and 500 mg of ABI 007 per $m^2$ of the patient's body surface over a duration of about 25–60 minutes. From 2 to 5 similar intra-arterial injections are then repeated at a time interval of 3–5 weeks one from another.

Tumors which have proved responsive to the described treatment are the squamocellular carcinomas, including certain tumors of the lung, head and neck, uterus and anal canal.

Preferably, the dispersion of microparticles in the physiological solution used for intra-arterial therapy of tumors contains from 200 to 300 mg of ABI 007 per $m^2$ of the patient's body surface for each administration, and the administration of each individual dose of the dispersion is effected over about 30 minutes.

Compared with the teachings of the aforestated previous known patents, it can be noted that, according to the present invention, doses of Paclitaxel are administered to the patient which are very much higher, and with infusion durations which are very much shorter, than is possible with intravenous administration, with favourable results (response percentage extremely high and surprising), observing very low toxicity in all cases.

Some examples relating to the treatment of tumors of different types and locations are described to clarify the understanding and the characteristics of the present invention.

EXAMPLE 1

A female patient (PR), 57 years of age, afflicted with pelvic recurrence of carcinoma of the anal canal, already previously treated by chemotherapy, radiotherapy and surgery and judged inoperable, is treated with four separate successive intra-arterial injections (at a distance of 4 weeks one from the other) into the internal iliac arteries, of dispersions of ABI 007 in physiological solution (Paclitaxel in microparticles of albumin) at doses of 220, 230, 250 and 275 mg per $m^2$ of body surface respectively.

The injected dispersions have a concentration of 6 mg of ABI 007 per ml of their solution.

The reduction in the tumor was followed by computerized tomography. Having observed an important tumor reduction and assuming that virtually complete regression of the mass had been achieved, a surgical intervention was performed and demonstrated the absence of the histological tumor.

EXAMPLE 2

To a female patient (ZN), 64 years of age, afflicted with voluminous neoplasia of the left half tongue, not previously subjected to any form of treatment, ABI 007 is administered in 4 successive cycles, at a dose of 210, 230, 200 and 200 mg/$m^2$ respectively, at a concentration of 4 mg/ml into the left lingual artery.

Response to the treatment was followed by clinical examination and magnetic resonance because of the presence of fixed dental prostheses.

Having observed important tumor regression, evaluated at 90% one month after the end of treatment, surgical intervention was proposed, and demonstrated histological absence of the tumor.

EXAMPLE 3

To a male patient (BP), 61 years of age, afflicted with carcinoma of the right hypopharynx, with metastasis at a right laterocervical lymph node not subjected to any previous treatment, ABI 007 is administered into the external carotid artery for 3 cycles, spaced apart by 4 weeks, at a dose of 240 mg/m$^2$ and at a concentration of 3 mg/ml. Having observed the therapeutic response by computerized tomography and clinical examination, multiple depth biopsies were performed in the hypopharynx, in the site previously occupied by the tumor, and demonstrated histological absence of neoplasia.

The lymphonodal metastasis had also decreased by more than 80% in dimensions and was removed by surgical intervention, with tumor presence at this level.

EXAMPLE 4

To a female patient (EP), 37 years of age, afflicted with recurrence of carcinoma of the anal canal, previously treated by radio-chemotherapy, ABI 007 was administered into the internal iliac arteries for 4 cycles spaced apart by 4 weeks, at a dose of 250 mg/m$^2$ per cycle, at a concentration of 7 mg/ml.

Having observed the therapeutic response by gynecological examination and computerized tomography, a new surgical intervention was proposed and demonstrated the histological absence of tumor.

EXAMPLE 5

To a male patient (GC), 59 years of age, afflicted with recurrence of carcinoma of the anal canal, previously treated by radio-chemotherapy, ABI 007 was administered into the internal iliac arteries at a dose of 200, 240 and 260 mg/m$^2$ respectively, at a concentration of 7.5 mg/ml.

Having observed the response by clinical examination and transrectal echoendosonography, a surgical intervention was proposed and demonstrated the histological absence of tumor.

What is claimed is:

1. A method of treating patients afflicted with a tumor sensitive to Paclitaxel, consisting of:

injecting into the artery feeding the region or organ associated with a tumor a dispersion in physiological solution containing from 190 to 500 mg of microparticles of Paclitaxel stabilized with albumin per m$^2$ of the patient's body surface, the injection having a duration ranging from 25 to 60 minutes; and then repeating the intra-arterial injection of the physiological solution containing the Paclitaxel microparticles from 2 to 5 times at intervals of 3–5 weeks between one infusion and the next.

2. A method treating a patient afflicted with a squamocellular carcinoma, consisting of:

injecting into the artery feeding the region or organ associated with this neoplasia a dispersion in physiological solution containing from 190 to 500 mg of microparticles of Paclitaxel stabilized with albumin per m$^2$ of the patient's body surface, the injection having a duration ranging from 25 to 60 minutes; and then repeating the intra-arterial injection of the physiological solution containing the Paclitaxel microparticles from 2 to 5 times at intervals of 3–5 weeks between one infusion and the next.

3. The method as claimed in claim 1, wherein the concentration of microparticles in the dispersion injected into the patient ranges from 200 to 300 mg per m$^2$ of the patient's body surface.

4. The method as claimed in claim 1, wherein the duration of the intra-arterial administration of the dispersion of microparticles is about 30 minutes.

5. A drug for treating solid tumors sensitive to Paclitaxel, comprising:

a dispersion of microparticles of Paclitaxel stabilized with albumin in a physiological solution in which the concentration of the microparticles ranges from 2 to 8 mg/ml of said solution, which effectively provides for the treatment of solid tumors sensitive to Paclitaxel.

6. The drug as claimed in claim 5, wherein the concentration of the microparticles in the dispersion ranges from 3 to 7.5 mg/ml of the solution.

7. The method as claimed in claim 2, wherein the concentration of microparticles in the dispersion injected into the patient ranges from 200 to 300 mg per m$^2$ of the patient's body surface.

8. The method as claimed in claim 2, wherein the duration of the intra-arterial administration of the dispersion of microparticles is about 30 minutes.

9. The method as claimed in claim 2, wherein the squamocellular carcinoma is located in the lungs, head, neck, uterus or anal canal.

* * * * *

UNITED STATES PATENT AND TRADEMARK OFFICE
CERTIFICATE OF CORRECTION

PATENT NO. : 6,652,884 B2
DATED : November 25, 2003
INVENTOR(S) : Marco Falciani Page 1 of 1

It is certified that error appears in the above-identified patent and that said Letters Patent is hereby corrected as shown below:

Title page,
Item [30], Foreign Application Priority Data, "May 17, 2000" should read
-- May 18, 2000 --.

Signed and Sealed this

Fifteenth Day of February, 2005

JON W. DUDAS
*Director of the United States Patent and Trademark Office*